(12) United States Patent
Wilcox

(10) Patent No.: US 8,926,546 B2
(45) Date of Patent: *Jan. 6, 2015

(54) C-SHAPED CROSS SECTION TUBULAR OPHTHALMIC IMPLANT FOR REDUCTION OF INTRAOCULAR PRESSURE IN GLAUCOMATOUS EYES AND METHOD OF USE

(71) Applicant: Aqueous Biomedical, Inc., Colorado Springs, CO (US)

(72) Inventor: Michael J. Wilcox, Colorado Springs, CO (US)

(73) Assignee: Aqueous Bomedical, Inc., Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/865,031

(22) Filed: Apr. 17, 2013

(65) Prior Publication Data

US 2013/0231602 A1 Sep. 5, 2013

Related U.S. Application Data

(63) Continuation of application No. 12/877,809, filed on Sep. 8, 2010, now Pat. No. 8,425,450, which is a continuation of application No. 11/181,326, filed on Jul. 14, 2005, now Pat. No. 7,806,847, which is a continuation-in-part of application No. 09/691,671, filed on Oct. 18, 2000, now Pat. No. 6,962,573.

(51) Int. Cl.
*A61M 5/00* (2006.01)
*A61F 9/007* (2006.01)
*A61F 9/00* (2006.01)

(52) U.S. Cl.
CPC ........... *A61F 9/00781* (2013.01); *A61F 9/0017* (2013.01)
USPC ............................................. 604/8

(58) Field of Classification Search
USPC .......... 604/27–29, 31–36, 521, 294; 606/101, 606/166, 153
See application file for complete search history.

(56) References Cited

U.S. PATENT DOCUMENTS

| | | | |
|---|---|---|---|
| 3,796,370 | A | 3/1974 | Speers et al. |
| 4,402,685 | A | 9/1983 | Buhler |
| 4,428,746 | A | 1/1984 | Mendez |
| 4,692,153 | A | 9/1987 | Berlin |

(Continued)

FOREIGN PATENT DOCUMENTS

| | | |
|---|---|---|
| JP | 6509732 | 11/1994 |
| JP | 8-117267 | 5/1996 |

OTHER PUBLICATIONS

Wilcox, Michael and Kadri, Omar A., Force and Geometry Determine Structure and Function of Glaucoma Filtration Capsules, Ophthalmalogica 2007; 221:238-243.

(Continued)

*Primary Examiner* — Philip R Wiest
(74) *Attorney, Agent, or Firm* — Polsinelli PC

(57) ABSTRACT

An implant may be used for implantation into tissue of a body. The implant includes an elongated conduit and a loop. The elongated conduit has an interior passageway for conducting fluid. The loop has an interior circumference with a fluid conducting channel formed therein. The channel is interconnected with the interior passageway for delivery of fluid between the channel and the interior passageway.

9 Claims, 9 Drawing Sheets

(56) References Cited

U.S. PATENT DOCUMENTS

| | | | |
|---|---|---|---|
| 4,883,468 A | 11/1989 | Kousai et al. | |
| 5,041,081 A | 8/1991 | Odrich | |
| 5,171,213 A | 12/1992 | Price, Jr. | |
| 5,178,604 A | 1/1993 | Baerveldt | |
| 5,195,978 A | 3/1993 | Schiffer | |
| 5,338,291 A | 8/1994 | Speckman | |
| 5,370,607 A | 12/1994 | Memmen | |
| 5,395,335 A | 3/1995 | Jang | |
| 5,417,651 A | 5/1995 | Guena et al. | |
| 5,433,701 A | 7/1995 | Rubinstein | |
| 5,501,232 A | 3/1996 | Ritleng | |
| 5,520,631 A | 5/1996 | Nordquist | |
| 5,558,630 A | 9/1996 | Fisher | |
| 5,601,094 A | 2/1997 | Reiss | |
| 5,704,907 A | 1/1998 | Nordquist | |
| 5,743,868 A | 4/1998 | Brown et al. | |
| 5,800,414 A | 9/1998 | Cazal | |
| 5,882,327 A | 3/1999 | Jacob | |
| 6,450,984 B1 | 9/2002 | Lynch | |
| 6,471,666 B1 * | 10/2002 | Odrich | 604/8 |
| 6,508,779 B1 | 1/2003 | Suson | |
| 6,589,203 B1 | 7/2003 | Mitrev | |
| 6,626,858 B2 | 9/2003 | Lynch | |
| 6,666,841 B2 | 12/2003 | Gharib | |
| 6,699,210 B2 | 3/2004 | Williams | |
| 6,783,544 B2 | 8/2004 | Lynch | |
| 6,827,699 B2 | 12/2004 | Lynch | |
| 6,827,700 B2 | 12/2004 | Lynch | |
| 6,955,656 B2 | 10/2005 | Bergheim | |
| 6,962,573 B1 | 11/2005 | Wilcox | |
| 6,979,328 B2 | 12/2005 | Baerveldt | |
| 6,981,958 B1 | 1/2006 | Gharib | |
| 7,135,009 B2 | 11/2006 | Tu | |
| 7,192,412 B1 | 3/2007 | Zhou | |
| 7,291,125 B2 | 11/2007 | Coronco | |
| 7,297,130 B2 | 11/2007 | Bergheim | |
| 7,806,847 B2 * | 10/2010 | Wilcox | 604/8 |

OTHER PUBLICATIONS

Wilcox et al., Performance of a New, Low-volume, High Surface Area Aqueous Shunt in Normal Rabbit Eyes, J. Glaucoma 9:74-82 (2000).

Wilcox, Michael J. and Minckler, Donald S., Hypothesis for Improving Accessory Filtration by Using Geometry, J. Glaucoma 3:244-247 (1994).

Wilcox, Michael J. et al.,. Pathophysiology of Artificial Aqueous Drainage in Primate Eyes with Molteno Implants, 3:140-151 (1994).

Preliminary Amendment dated Sep. 8, 2010, U.S. Appl. No. 12/877,809, 4 pages.

Office Action dated Dec. 8, 2011, U.S. Appl. No. 12/877,809, 7 pages.

Amendment dated Mar. 8, 2012, U.S. Appl. No. 12/877,809, 8 pages.

Final Office Action dated Aug. 31, 2012, U.S. Appl. No. 12/877,809, 9 pages.

Amendment After Final dated Nov. 19, 2012, 8 pages.

Notice of Allowance and Fee(s) Due dated Dec. 19, 2012, U.S. Appl. No. 12/877,809, 8 pages.

Non-Final Office Action dated Apr. 30, 2007, U.S. Appl. No. 11/181,326, 5 pages.

Amendment and Response to Office Action dated Aug. 30, 2007, U.S. Appl. No. 11/181,326, 5 pages.

Final Office Action dated Nov. 8, 2007, U.S. Appl. No. 11/181,326, 6 pages.

Amendment and Response to Office Action with Request for Continued Examination, U.S. Appl. No. 11/181,326, 5 pages.

Request for Continued Examination dated May 8, 2008, U.S. Appl. No. 11/181,326, 1 page.

Non-Final Office Action dated Jun. 2, 2008, U.S. Appl. No. 11/181,326, 6 pages.

Amendment and Response to Office Action dated Nov. 3, 2008, U.S. Appl. No. 11/181,326, 5 pages.

Supplemental Amendment and Response to Office Action dated Jan. 5, 2009, U.S. Appl. No. 11/181,326, 6 pages.

Notice of Allowance and Fees Due dated Mar. 2, 2009, U.S. Appl. No. 11/181,326, 4 pages.

Request for Continued Examination dated Jun. 2, 2009, U.S. Appl. No. 11/181,326, 1 page.

Notice of Allowance and Fees Due dated Jul. 13, 2009, U.S. Appl. No. 11/181,326, 4 pages.

Request for Continued Examination dated Oct. 13, 2009, U.S. Appl. No. 11/181,326, 1 page.

Notice of Allowances and Fees Due dated Jan. 12, 2010, U.S. Appl. No. 11/181,326, 4 pages.

Request for Continued Examination dated Apr. 12, 2010, U.S. Appl. No. 11/181,326, 1 page.

Notice of Allowance and Fees Due dated May 28, 2010, U.S. Appl. No. 11/181,326, 4 pages.

Office Action dated Jul. 5, 2002, U.S. Appl. No. 09/691,671, 9 pages.

Amendment A dated Nov. 13, 2002, U.S. Appl. No. 09/691,671, 7 pages.

Office Action dated Jan. 28, 2003, U.S. Appl. No. 09/691,671, 4 pages.

Amendment B dated Feb. 21, 2003, U.S. Appl. No. 09/691,671, 7 pages.

Office Action (Non-Compliant Notice) dated May 20, 2003, U.S. Appl. No. 09/691,671, 4 pages.

Amendment C dated Jun. 16, 2003, U.S. Appl. No. 09/691,671, 11 pages.

Response to Non-Compliant Notice dated Jan. 16, 2004, U.S. Appl. No. 09/691,671, 11 pages.

Final Office Action dated Apr. 8, 2004, U.S. Appl. No. 09/691,671, 8 pages.

Notice of Appeal dated May 3, 2004, U.S. Appl. No. 09/691,671, 1 page.

Appeal Brief dated Jun. 14, 2004, U.S. Appl. No. 09/691,671, 14 pages.

Notice of Allowance and Fee(s) Due dated Feb. 10, 2005, U.S. Appl. No. 09/691,671, 6 pages.

* cited by examiner

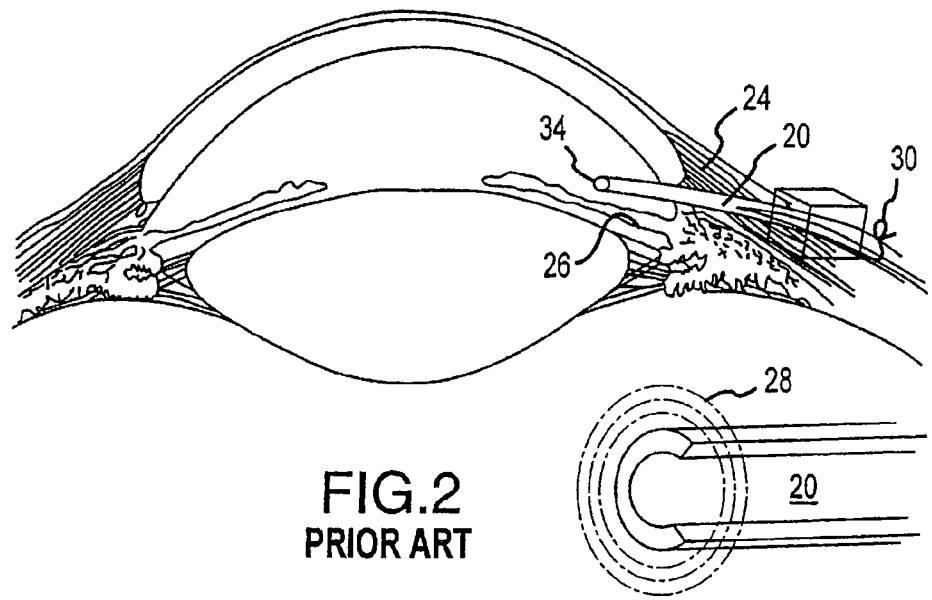
FIG. 2
PRIOR ART
FIG. 1
PRIOR ART
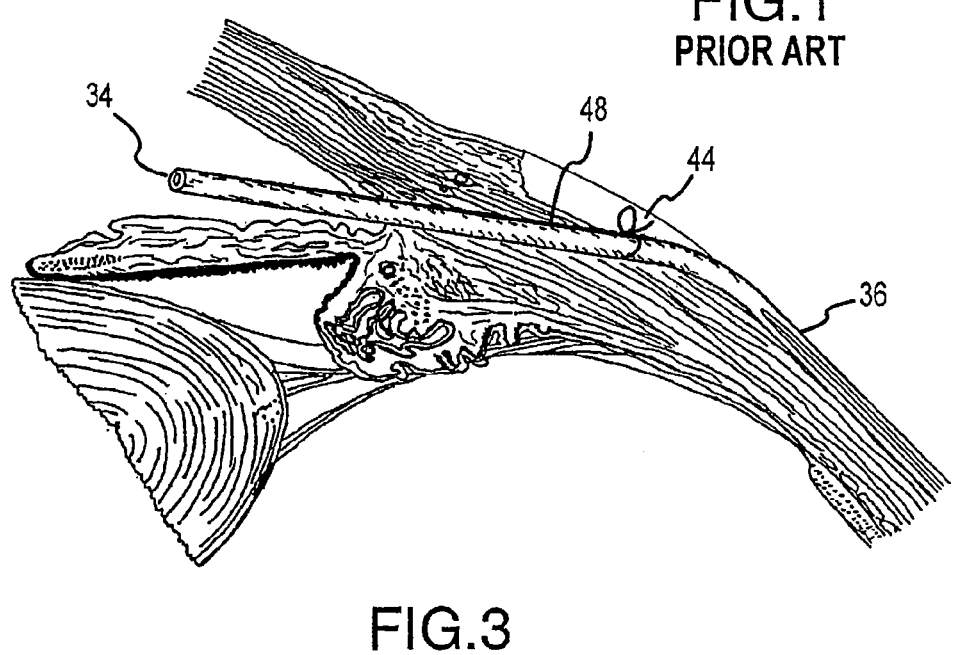
FIG. 3

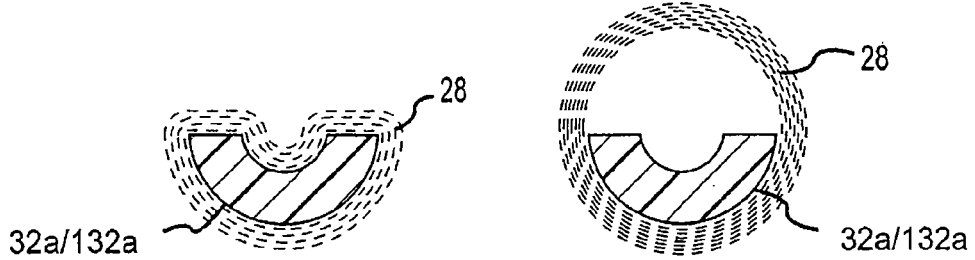
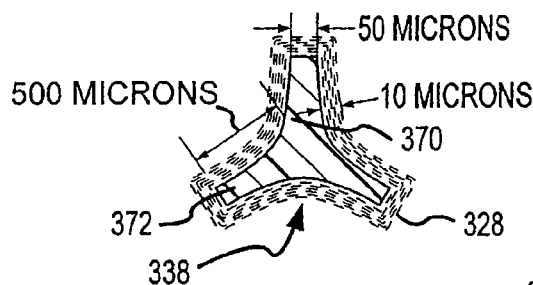 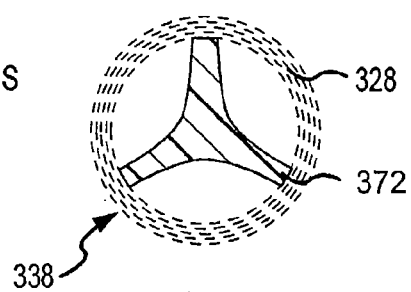
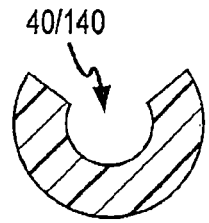 
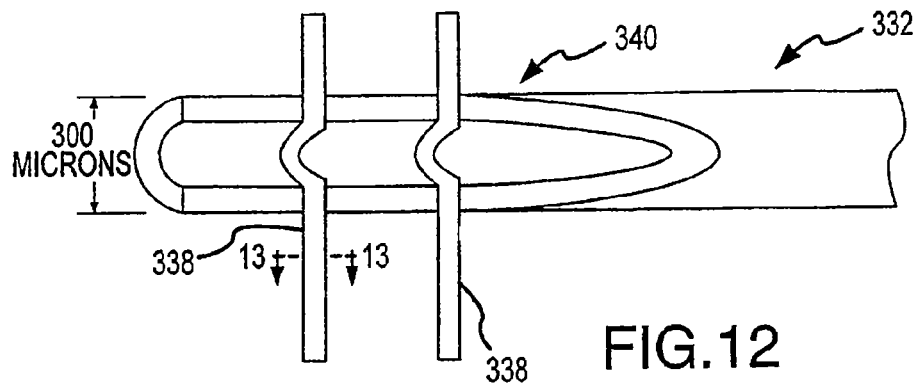

C-SHAPED CROSS SECTION TUBULAR OPHTHALMIC IMPLANT FOR REDUCTION OF INTRAOCULAR PRESSURE IN GLAUCOMATOUS EYES AND METHOD OF USE

CROSS REFERENCE

This application is a continuation of U.S. application Ser. No. 12/877,809, filed Sep. 8, 2010, now U.S. Pat. No. 8,425,450, which is a continuation of U.S. application Ser. No. 11/181,326, filed Jul. 14, 2005, now U.S. Pat. No. 7,806,847, which application is a continuation-in-part of U.S. application Ser. No. 09/691,671, filed on Oct. 18, 2000, now U.S. Pat. No. 6,962,573, all of which are hereby incorporated by reference herein in their entireties.

BACKGROUND

Glaucoma is a disease characterized by high pressure inside the eye, leading to the loss of retinal nerve fibers with a corresponding loss of vision. Glaucoma, therefore, is a disease affecting the optic nerve, the nerve bundle which carries visual information to the brain.

The eyeball is basically a rigid sphere filled with fluid. Positive pressure inside the eye is needed to keep the retina attached to the back of the eye. Pressure is maintained by fluid production from a bilayer of cells on top of the ciliary body, which is located adjacent to the iris root in the eye. This clear fluid, called aqueous humor, carries nutrients to the lens and cornea of the eye, both of which have no blood supply. The shape of the front part of the eye is maintained by aqueous humor production. The ciliary body is located behind the colored part of the eye (iris). Fibrous strands called zonule fibers attached to the ciliary body support the lens. Tension from the rigid structure of the eye, transferred to these zonules, deforms the lens and focuses the image onto the retina. Radial muscles behind the ciliary body contract and release tension on the zonules allowing the lens to round up and focus near images onto the retina. Aqueous humor flows into the front of the eye through the pupil and drains out of the eye through the trabecular meshwork. The trabecular meshwork is a spongy mass of tiny channels located in the drainage angle, between the clear covering of the eye (cornea) and the colored part (iris) at the location where the iris meets the white outer covering of the eye (sclera). The fluid drains from the meshwork into a small canal, called Schlemm's canal, which is connected to the bloodstream at the venous return from the eye. Aqueous humor is produced by the ciliary body and removed from the eye at a constant rate (about 1.0 tsp or 5.0 ml per day) to maintain a constant pressure in the front (anterior) chamber of the eye. While pressure in the eye varies throughout the day, the average pressure within the eye is 10 mm Hg to 15 mm Hg. If the resistance to fluid flow increases or the amount of fluid generated exceeds the capacity of the meshwork to vent it, pressure inside the eye increases, similar to over-inflating a tire. The higher the pressure inside the eye, the greater the chance of damage to the optic nerve. Glaucoma is the leading cause of blindness in third world countries, and the leading cause of preventable blindness in industrial countries. It affects approximately 2% of the entire population; blacks and native Americans are disproportionately represented, with elevated occurrence of the disease. Early signs of the disease are often observed as enlargement and cupping of the physiological blind spot which is the point where the optic nerve leaves the eyeball and projects to the brain. Blind spots in the superior and inferior visual fields (called arcuate scotomas) correspond to the loss of nerve cells. In later stages, more visual field losses eventually end in total blindness. If the drainage angle becomes blocked, fluid pressure transferred throughout the eye increases, damaging the optic nerve—the part of the eye responsible for transforming images into impulses the brain can translate. This damage results in partial or complete blindness.

In acute angle-closure glaucoma, eye pressure builds up rapidly. This type of glaucoma commonly occurs in individuals who have narrow anterior chamber angles. In these cases, aqueous fluid behind the iris cannot pass through the pupil and pushes the iris forward, preventing aqueous drainage through the angle. It is as though a sheet of paper floating near a drain suddenly drops over the opening and blocks the flow out of the sink. In cases of acute angle closure glaucoma, one may experience blurred vision, halos around lights, pain, nausea, and vomiting. If pressure within the eye is not immediately relieved, blindness may result in a matter of days. Migration of pigmented epithelial cells in the eye, either congenital or following blunt trauma, can occlude angle structures quickly elevating pressure in the eye. Primary open-angle glaucoma has a longer time course and many components that exacerbate the condition. The end effect is the same. Secondary glaucoma can occur from inflammation, degeneration, trauma, or tumor growth within the eye. Certain medications are also reported to cause secondary glaucoma. In summary, the disease glaucoma is a plethora of conditions that elevate intraocular pressure. Left uncontrolled, high intraocular pressure leads to blindness.

In the detection of glaucoma, measuring the pressure in the eye by itself does not give a diagnosis of glaucoma. Of more importance is the direct observation of damage to the optic nerve itself and sometimes the nerve fiber layer of the retina. Quantifying a loss of vision in part of the visual field consistent with observed nerve fiber loss is the true definitive diagnosis for glaucoma. Loss of nerve fibers caused by glaucoma cannot be reversed. Therefore, the goal in the management of glaucoma is to reduce the intraocular pressure to the point whereby the remaining healthy nerve fibers are able to maintain function.

Surgical treatment of glaucoma using a shunt implant to vent aqueous humor from the anterior chamber to a subconjunctival bleb is warranted in some cases. To date, all the currently available shunt implants consist of a tube or conduit attached to the surface of a large plate. The conduit carries fluid from the anterior chamber to the surface of the plate. A cellular capsule forms around that plate and once inflated with aqueous humor from the anterior chamber forms a large blister or bleb around the plate on the outer surface of the eye. The geometry of the blister's surface takes on the shape of the plate. The cellular capsule forming the bleb wall filters fluid to the subconjunctival space and provides resistance to fluid flow so pressure in the eye will not be too low.

Our research shows that a large volume blister causes most of the postsurgical complications. A hemispherical blister or any large cavity is an ideal geometry for maximizing volume while minimizing surface area. Since the bleb wall filters fluid, the surface area and hydraulic conductivity of that filter are the important parameters in its function. In filtration across a membrane, the pressure across the filtration capsule and the surface area of the filtration capsule determine how much fluid will filter across the membrane. Since increasing surface area is the goal, a spherical design is an adverse geometry for this goal.

Another problem with spherical blister geometry is that surface tension is proportional to the radius of a blister (Laplace's law). The larger the force applied to this cellular capsule, the more the membrane will stretch out until the cohesive force of the capsule can no longer match the force provided by pressure, in which case it will rupture causing the pressure to be too low. The body's reaction to applied force is to reinforce the capsule with collagen. All large plate devices experience this condition and require a maturation period during which the capsule thickens but a thick capsule makes it less effective at filtering or venting fluid and sometimes fails early due to the build up of fibrous tissue in the capsule.

SUMMARY OF THE INVENTION

The present invention comprises an implant for the reduction of intraocular pressure. The novelty of the present invention is a post-surgical ability to customize the total surface area of the implant, increasing fluid filtration by increasing surface area without the need of further surgery or an additional implant. After post-surgical intraocular pressure has been determined, a ligature or series of ligatures located at intact portions along the length of the implant situated between open, cross-sectional portions can simply be removed. The present invention also comprises an implant anchor attachable to the sclera at the limbus and having the advantage of preventing migration of the implant into the anterior chamber. The invention provides a further thirteen-fold reduction in bleb diameter as compared to the prior art resulting in a thinner capsule with hydraulic conductivity higher than capsules around implants of any prior art. Such a capsule, in the best case only one cell layer thick, has the further advantage that the resultant structure approaches the dimensions of the normal trabecular meshwork in a human eye. The small diameter of the present invention provides an implant with a resultant low surface tension on the wall of the capsule with the advantage that fibrosis is minimized, thereby allowing a constant filtration rate of aqueous and reduction in intraocular pressure to a safe and stabilized level.

The implant consists of a cylindrical tube with a diameter of approximately four hundred micrometers and with an intact proximal end and a distal end for implantation into an eye. The proximal end serves as a conduit for aqueous humor to bypass angle structures. The distal end serves as a nidus for cell deposition to form a filtration capsule that vents fluid and reduces pressure in the eye. Where a lateral portion of the tube is removed, the interior of the tube is exposed creating an open side walled portion of the tube. A cross section of the open side walled portion normal to the length of the tube is in the shape of an arch. The tube may further comprise a series of lateral portions where the sidewall of the tube is removed. Removed lateral portions are located serially along the length of the tube and separated by whole cylindrical portions. Lateral portions are situated in a non-overlapping configuration. A ligature is tied to each of the whole cylindrical portions whereby flow through the whole cylindrical portions is prevented until the ligature is released. A second form of anchor comprises a split end of the tube wherein the end of the tube is split multiple times.

The invention may also incorporate a portion, scalloped (or asterisk-shaped) in cross section, extending outwardly from at least one side of the exposed interior of the tube to further serve as a nidus for cell growth and capsule formation. The scalloped portion has a radius of 500 microns from the center to the tip of the scallop, a tip width of 50 microns, and preferably extends between 10 millimeters and 30 millimeters in a normal direction from the tube. If the capsule or bleb is deposited onto a smooth, solid surface, pressure from the anterior chamber may not always be sufficient to separate the capsule from the smooth, solid surface and inflate a volume in the subconjunctival space. If a bleb does not form or if the capsule remains attached to the implant material, it will not vent fluid and will not become functional.

The method of the present invention for reducing intraocular pressure by creating a cylindrical bleb for producing improved accessory filtration comprises the steps of implanting a cylindrical tube having a proximal end and distal end. The proximal end of the tube is intact and serves as a conduit for aqueous humor to bypass the angle structures. The distal portion of the cylindrical tube has the side wall removed to allow fibrous tissue to form on its surface. Once this fibrous capsule has formed, a ligature around the intact portion of the tube is removed. Pressurized aqueous humor from the anterior chamber elevates the capsule into a functional bleb that filters aqueous humor into the extracellular space underneath the conjunctiva. This fluid is eventually removed from the eye and reenters the vascular circulation. Installation consists of the steps of incising the conjunctiva, elevating the conjunctiva from the sclera, implanting the distal portion of the cylindrical tube under the conjunctiva, anchoring the proximal end of the cylindrical tube to the sclera at the limbus, inserting the proximal, intact end of the tube into the anterior chamber through a needle track, ligating the proximal end to prevent hypotony, allowing approximately one week for cell growth around the tube, releasing a ligature around the proximal end after approximately one week to inflate the bleb, measuring the intraocular pressure to determine if additional drainage is required, if additional drainage is required, releasing additional ligatures whereby additional blebs are inflated.

DESCRIPTION OF THE DRAWINGS

FIG. 1 is a schematic representation of a prior art implant.

FIG. 2 is a schematic representation of the anterior segment of an eye with a prior art implant in place.

FIG. 3 is a cross section of the ciliary root and iris of an eye and an implant in place.

FIG. 10 is a cross section of a C-shaped distal nidus of the implant of FIGS. 4 and 5 during capsule (or bleb) formation taken along lines 10-10.

FIG. 11 is a view similar to that of FIG. 10 but showing the inflation of the capsule following removal of the ligature.

FIG. 12 is a schematic representation of another embodiment of the invention employing stripped nidus portions extending laterally from a cutaway portion of the implant.

FIG. 13 is a cross section of a scalloped or flat portion of the FIG. 12 implant taken along lines 13-13 of FIG. 12 during capsule (or bleb) formation.

FIG. 14 is a view similar to that of FIG. 13 but showing the inflation of the capsule following removal of the ligature.

FIG. 15 is a cross section of an implant's lateral nidus projection taken along lines 15-15 of FIGS. 4 and 5.

FIG. 16 is a cross section of the implant's lateral nidus projection taken along lines 16-16 of FIGS. 4 and 5.

DETAILED DESCRIPTION

Figure 4:
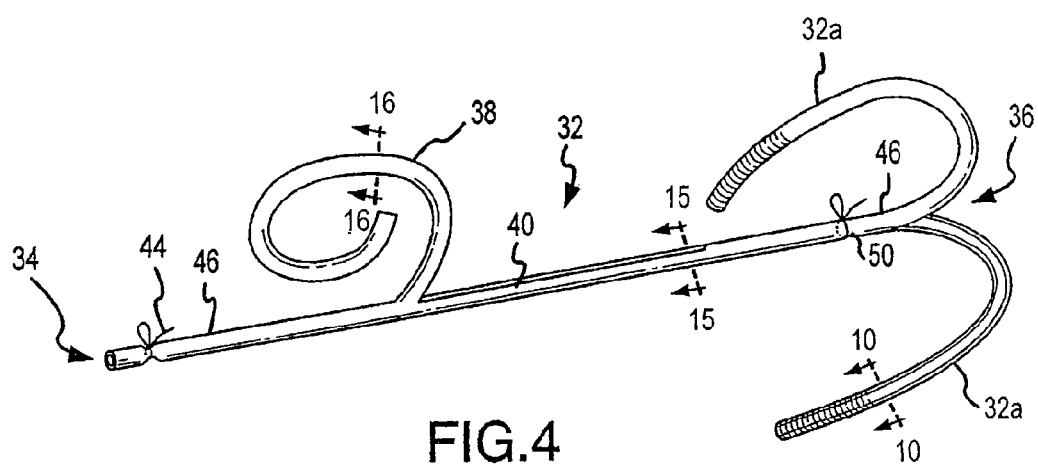
FIG. 4 is a schematic representation of a double-section, bifurcated implant.

Referring now to FIG. 4 of the drawings, there is shown a schematic representation of the ophthalmic implant, cylindrical tube 32, with the proximal end 34 shown on the left and the distal end 36 shown on the right. It is to be noted that tube 32 may be and includes tubes of a cross-sectional shape other than circular, e.g. triangular, rectangular, pentagonal, L-shaped, etc. This is because the capsule formed around the tube when the capsule is inflated will be essentially a cylindrical shape as it is inflated by fluid. In addition, tube 32 may be of any suitable material. One example of a suitable material is silicone.

In practice, the conjunctiva is incised about 3 mm from the limbus and the conjunctiva is elevated by blunt dissection 10-12 mm back so that the longer distal end of the implant can be pushed into the pocket so formed. Through this same incision, a needle track is made entering the anterior chamber just in front of the iris. The proximal end 34 is inserted through this needle track 48, shown in FIG. 3, made by a 27 gauge needle. The small gauge ensures that limbal tissues adhere to the tube 32 without leakage so that intraocular pressure from aqueous humor can reform the anterior chamber. The tube serves as a permanent conduit for passage of aqueous humor past the angle structures. The distal tubing serves as a nidus for the growth of fibrous, permeable tissue. Once elevated from the tube 32 this fibrous tissue forms a filtration capsule that drains aqueous humor into subconjunctival tissue. Venting this fluid is controlled by the hydraulic resistance of the capsule and controls intraocular pressure preventing further damage to the optic nerve, which is characteristic of the disease, glaucoma.

Figure 7:
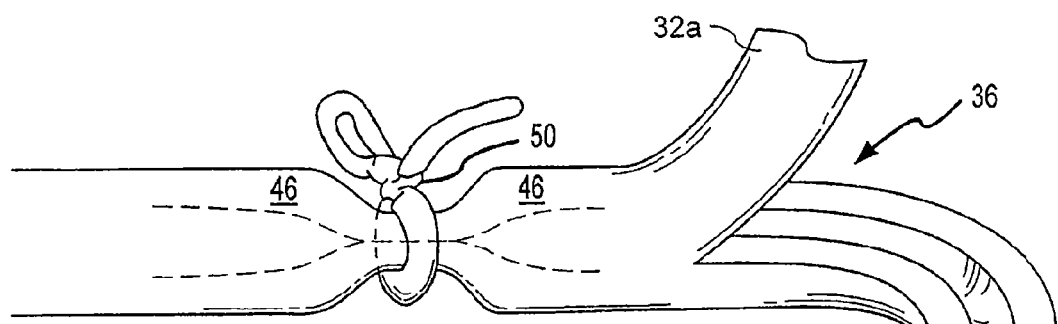
FIG. 7 is an enlarged fragmentary view of the distal end of the implant of FIGS. 4 and 5.

The inserted tube may be made of silicone or any other suitable, flexible material. Flexible material is chosen to prevent erosion of eye tissues in contact with the implant. The proximal end 34 comprises a whole cylindrical portion 46 which is ligated, i.e., tied off with ligature 44 as shown in FIGS. 3 and 7. The ligatures may comprise slip knots for ease of removal after insertion of the implant. It is to be noted that any equivalent to a slip knot or lysis with a laser, which would allow simple opening of a closed off portion could be used. Ligature 44 also serves to anchor tube 32 to the sclera at the limbus where the tube enters the anterior chamber through needle track 48. As with most surgical intervention, in the early postoperative days, there is a seton effect, where aqueous leakage occurs along the path 48 where the implant 32 enters the anterior chamber. It is during this period that the eye is at risk due to hypotony, i.e., low pressure and possible retinal detachment. Therefore, a newly installed tube is ligated initially, until a proper capsule can grow around the implant. A lesser desired alternative to ligating the tube is use of a soluble plug surrounding the tube. The weakest tissue adhesion point in the implant 32 is between the fibrous cellular capsule and the tube 32. The implant lateral portion 38 is peeled back (similar to peeling a banana) or otherwise removed along the open side 40 of the implant to form a nidus for fibrous cell growth along C-shaped cross sections as shown in FIGS. 15 and 16. Once ligature 44 is released, pressurized aqueous will lift the capsule away from the tube 32 and form a bleb 28. FIG. 10 shows the fibrous capsule 28 prior to release of ligature 44 and FIG. 11 shows the fibrous capsule 28 as inflated after release of ligature 44. The tube 32 remains free-floating within the bleb to prevent constriction, collapse, or adhesions forming inside the bleb. Alternatively, the distal tube 32 may be made of dissolvable material which is eventually sloughed off. The proximal portion must remain intact and permanently in place or else the tight limbal tissues will occlude the opening through the angle structures and aqueous passage will be blocked.

The tube of the present embodiment is bifurcated at distal end 36, FIG. 4. Bifurcated portions 32a and lateral portion 38 may be shaped as shown in FIG. 10, 13, 15, or 16 or any other suitable shape. Bifurcated portions 32a of 36 and lateral portion 38 in FIG. 4 serve as nidi for fibrous tissue growth 28 as shown in FIG. 10. After 5-7 days the capsule 28 has had sufficient time to form with an appropriate thickness. Elevation of the capsule from the implant by pressurized aqueous forms a bleb that filters aqueous into subconjunctival tissues. Bifurcated portions 32a FIG. 4 serve as a second anchor after a bleb is formed around these bifurcated portions. Thereafter, ligature 44 (FIG. 4 and FIG. 7) is released thereby inflating capsule 28, FIG. 11, and allowing aqueous to pass from the anterior chamber to subconjunctival tissue. Capsule 28 is the fibrous tissue growth that provides resistance to fluid flow.

Figure 5:
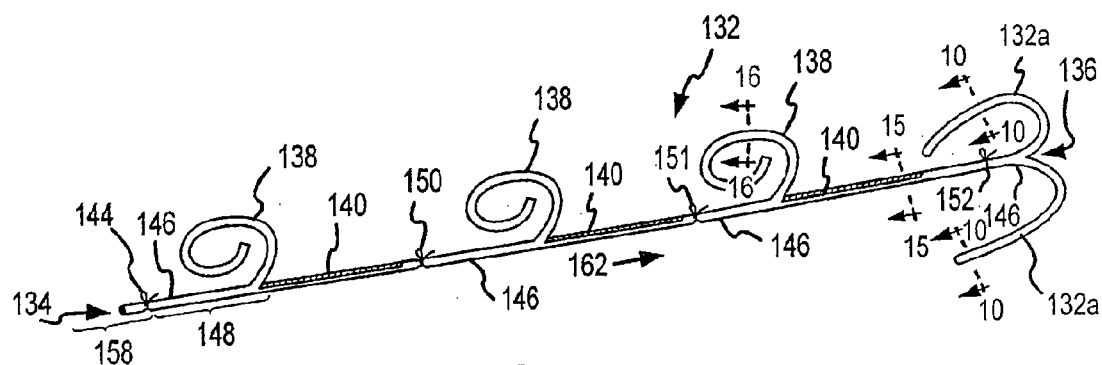
FIG. 5 is a schematic representation of multiple-section, bifurcated implant.
Figure 6:
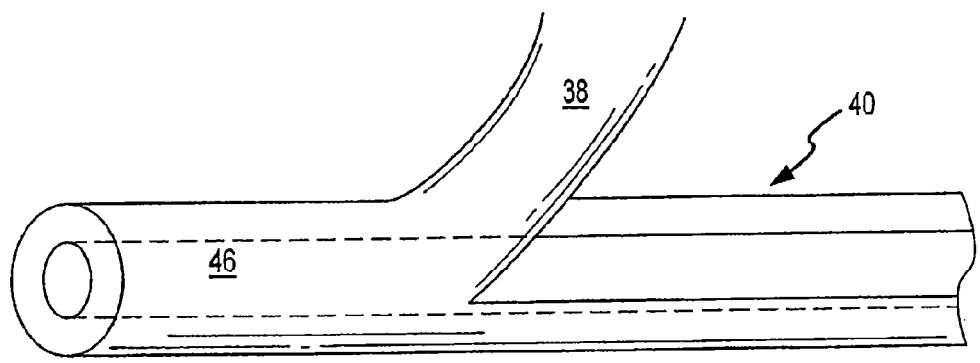
FIG. 6 is an enlarged fragmentary view of the junction between the main tubular body of the implant and a lateral peeled back portion.

Referring to FIG. 5, the second embodiment reflects a replication of the middle section of the first embodiment of FIG. 4 including ligature 144 tied around intact cylindrical portion 146. An advantage of the multiple whole cylindrical sections 146 and the associated ligatures 144, 150, 151 and 152 of the FIG. 5 embodiment of the invention is that the length of the operable implant, i.e. the inflated capsule portion may be increased as required by removing a ligature or a plurality of ligatures section-by-section in series by simply removing the ligatures in a manner well-known to one skilled in the art, in this case, an ophthalmologist. The present invention offers a post-surgical ability to customize the total surface area of the implant by increasing the functional surface area without the need of further surgery or an additional implant by simply removing a ligature 44 (FIG. 4) or series of ligatures 144, 150, 151, and/or 152 from the whole cylinder portion(s) 146 (FIG. 5) after post-surgical intraocular pressure has been determined. It can readily be seen by one skilled in the art that the tube may contain any reasonable number of peeled back portions 138 and resulting open sides 140.

Figure 8:
FIG. 8 is a schematic representation of a quadricated implant.
Figure 9:
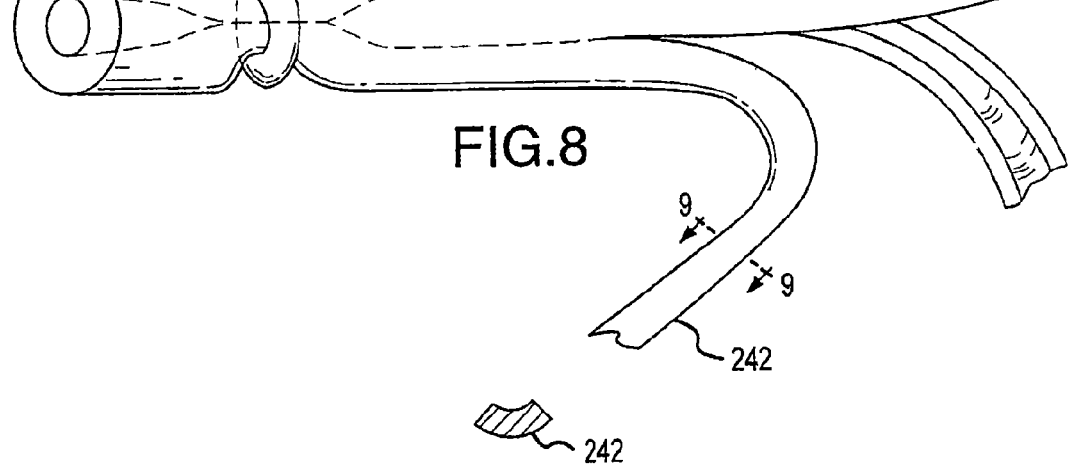
FIG. 9 is a cross section of a quadricated, C-shaped strand of the FIG. 8 implant taken along lines 9-9 of FIG. 8.

FIG. 8 shows a third embodiment of the invention similar in all respects to the first and second embodiments except the distal end 236 is quadricated, i.e. split into four sections 242 rather than two sections 32a. It can readily be seen by one skilled in the art that the distal end may be split into any reasonable number of sections. The purpose of forming the split end sections 32a (FIG. 7), 242 (FIG. 8), and the peeled back lateral portions 38 (FIG. 4) is to allow a greater surface area but minimal diameter of inflated capsule. It does not matter that the nidi formed by the split ends become increasingly smaller in cross section. As the number of splits increase, the diameter of the bleb formed will be smaller in diameter and further reduce surface tension on the capsule, resulting in a thinner capsule wall. The thickest part of the capsule, forming around the C-shaped section 40 (FIG. 4), is only approximately three cells in thickness.

FIGS. 12-14 show a fourth embodiment of the invention. This embodiment includes scalloped nidus 338 extending from either side of the open-sided, C-shaped section 340

(FIG. 12). Scalloped nidus 338 may be attached to main body 340 of the implant by any well-known means. A cross section of scalloped nidus 338 is shown in FIGS. 13 and 14. Bleb 328 is shown formed around nidus 338 in FIG. 13. Scalloped portion 338 includes central or hub portion 370 and tip portions 372. Scalloped portion 338 has a radius of 500 microns from the center to the outer tip 372 of the scallop, a tip width of 50 microns, and preferably extends up to 20 millimeters in a normal direction from the tube depending upon the requirements determined by the ophthalmologist. The advantage of the scalloped geometry is that, if the capsule or bleb is deposited onto a smooth, solid surface, pressure from the anterior chamber may not always be sufficient to separate the capsule from a smooth, solid surface and inflate a volume in the subconjunctival space. If an inflated capsule does not form or if the capsule remains attached to the implant material, it will not vent fluid and will not become functional. The scallop simply makes it easier for the tissue to release form the nidus once pressure is applied following ligature release. The number of scallops is a matter of choice, however 3, 4, 5, or 6 scallops is a reasonable number. Likewise, other forms providing a wave-like perimeter, such that the length of the perimeter is greater than the diameter of the form multiplied by pi, are within the scope of the present invention.

The method of the present invention for reducing intraocular pressure by creating a cylindrical bleb for producing improved accessory filtration comprises the steps of implanting a cylindrical tube having a proximal end and distal end, the distal portion of the cylindrical tube side wall being removed, into an eye to serve as a nidus for tissue deposition onto the implant surface. Later, when pressurized aqueous is applied following ligature release, this tissue everts forming a filtration membrane with a cylindrical geometry and a conduit of aqueous humor to bypass angle structures consists of the steps of implanting the distal portion of the cylindrical tube under the conjunctiva, anchoring the proximal end of the cylindrical tube to the limbus, inserting the proximal, intact end of the tube into the anterior chamber through a needle track, ligating the distal end to prevent hypotony, allowing approximately one week for a bleb to grow around the tube, releasing a ligature around the proximal end after approximately one week to inflate the bleb, measuring the intraocular pressure to determine if additional drainage is required, if additional drainage is required, releasing additional ligatures whereby additional blebs are inflated.

Those with skill in the art of surgical treatment of glaucoma will readily see the invention's simplicity and flexibility. All currently available shunt implants function by using a conduit to maintain an open passage through the trabecular meshwork from the anterior chamber of the eye to a subconjunctival bleb (medical term for a "blister"). A fibrous capsule forms the walls of that bleb and provides resistance to aqueous flow and prevents hypotony. A hemisphere (blister) is an ideal geometry for minimizing surface area while maximizing volume. This is an adverse design because increasing the surface area is the goal so that aqueous can be vented to the orbit and control pressure inside the eye. The other problem with the spherical blister design is that surface tension is proportional to the radius (Laplace's law). The larger the force applied to this cellular capsule, the more the membrane will stretch out until the cohesive force of the capsule cannot match the applied force, in which case the capsule would rupture like a balloon. The body's reaction to applied force is to reinforce the capsule with collagen. Increasing collagen deposition makes the capsule thicker and less effective at filtering fluid. Our innovation is that we use geometry to reduce the force per millimeter stress on the capsule and decrease collagen deposition in the filtration capsule. Current evolution of these large-plate shunt devices suggests that the designers do not share this opinion. That is why our design is different. Thus the reader will see that the implant and method of reducing intraocular pressure of the present invention provides a more effective and customizable, yet economical solution for reduction of intraocular pressure.

The parent to this application describes the only glaucoma shunt implant that changes the entire geometry of the filtration capsule from a blister to a small diameter cylindrical shape. The mechanism by which this principle works is an implementation of Laplace's law that reduces surface tension on the capsule wall by using a small diameter cylindrical shape and, therefore, remains thin and hydraulically very efficient. The present application describes a design that employs the principles we have demonstrated in our own research, namely reduced channel diameter that provides decreased surface tension and increased filtration surface area using a cylindrical geometry rather than a large plate.

Figure 17:
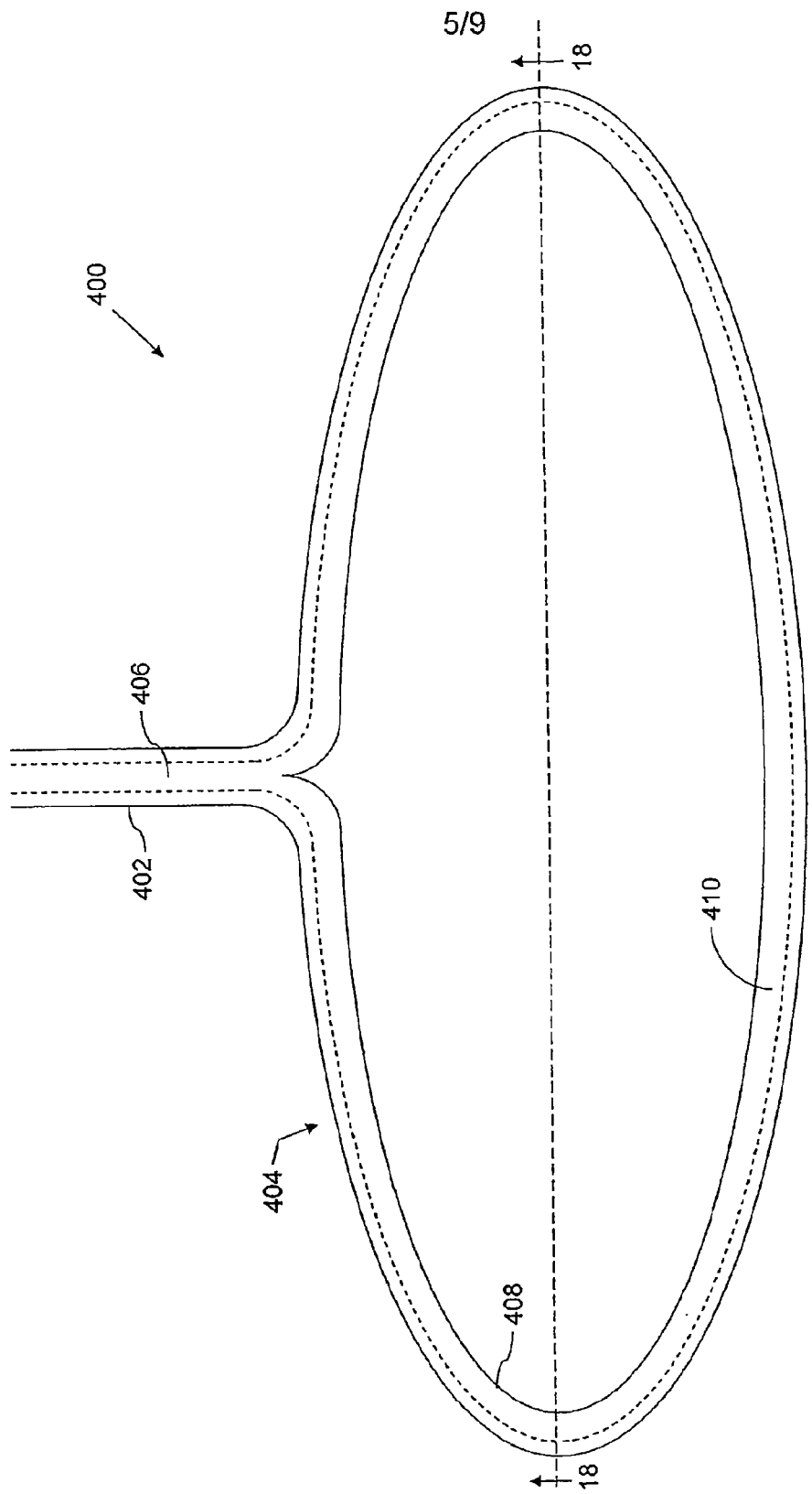
FIG. 17 is a diagram of an alternate embodiment of the present invention implant.
Figure 18:
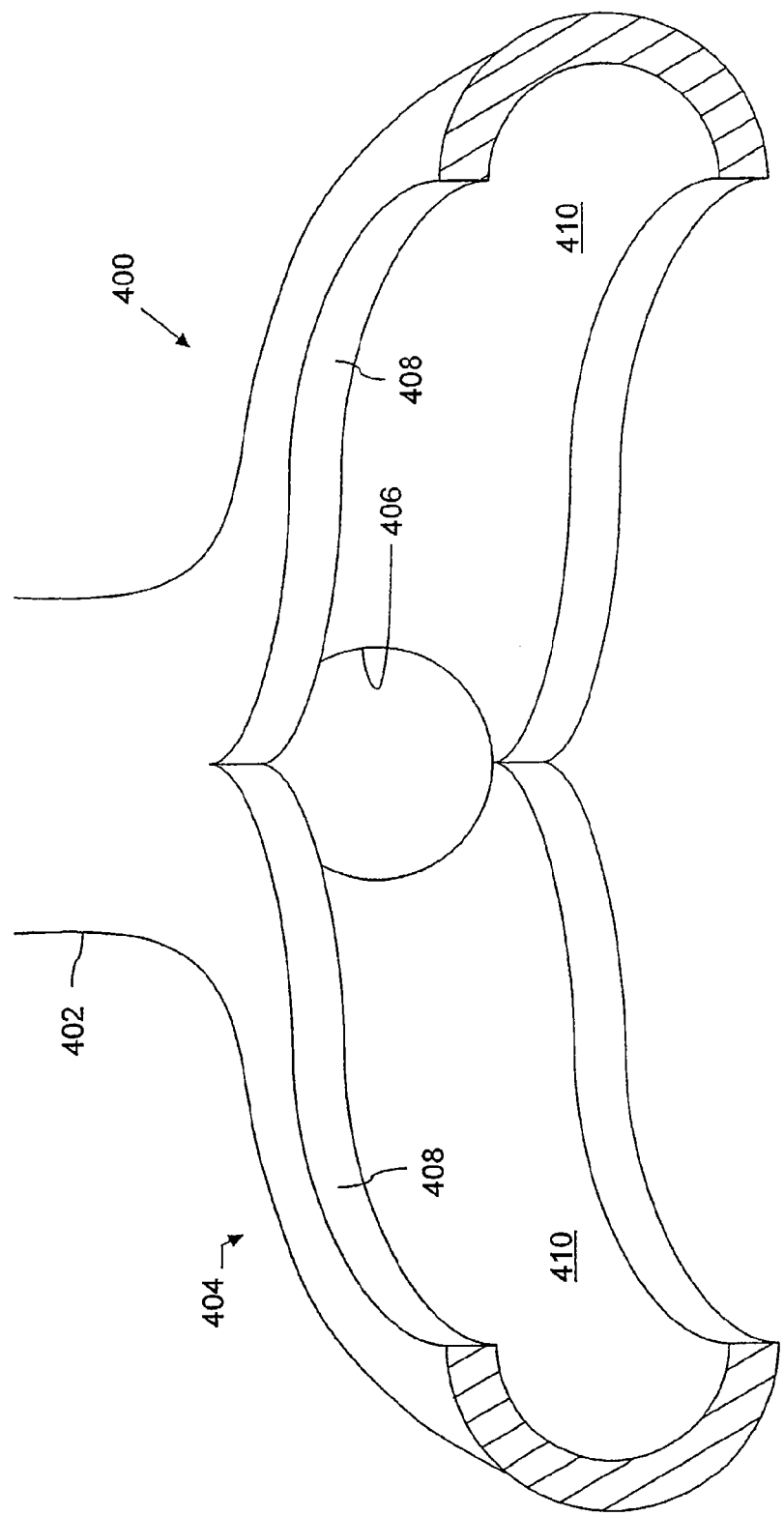
FIG. 18 is a cross section of the loop taken along lines 18-18 of FIG. 17.

FIGS. 17 and 18 show an alternate embodiment of implant 400 for implantation into tissue of a body. In one embodiment, implant 400 includes elongated conduit 402 and loop 404. Conduit 402 has an interior passageway 406 (shown in dashed lines) for conducting fluid.

Loop 404 has an interior circumference 408 and an exterior circumference 409. In the illustrated embodiment, interior circumference 408 has a fluid conducting channel 410 (shown in dashed lines) formed therein. Channel 410 is interconnected with interior passageway 406 for delivery of fluid between channel 410 and interior passageway 406. Alternatively stated, channel 410 is in fluid conducting communication with interior passageway 406 of conduit 402. As a result, fluid is conducted along channel 410 and into passageway 406 or, alternatively, along passageway 406 and into channel 410. Additional structures may intervene between channel 410 and passageway 406 as long as fluid flow is conducted, or guided, between the two.

Although the figures show the fluid conducting channel 410 embodied in the interior circumference 408, the fluid conducting channel 410 may alternatively be implemented in the exterior circumference 409 or any other surface of loop 404.

In one embodiment, loop 404 includes means for implementing the formation of at least one aqueous filtration bleb in the tissue. The structure of loop 404 within the tissue causes the formation of the at least one aqueous filtration bleb in the tissue.

Loop 404 may be interconnected with, or carried by, conduit 402 in any manner. For example, loop 404 may extend from conduit 402, as illustrated in FIGS. 17 and 18, or be attached to conduit 402, as shown in FIGS. 19-21.

Figure 19:
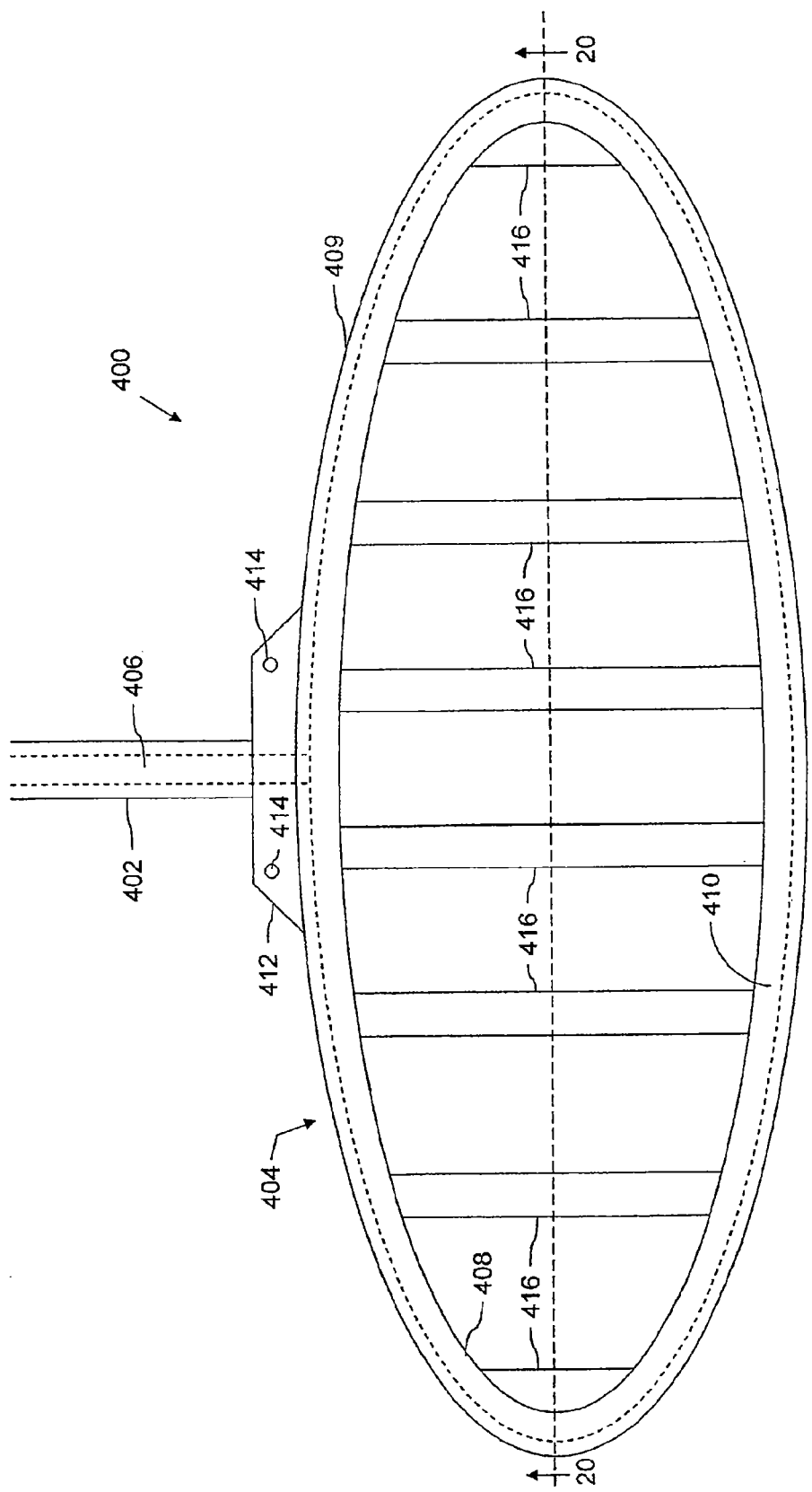
FIG. 19 is a diagram of an alternate embodiment of the implant shown in FIGS. 17 and 18.
Figure 20:
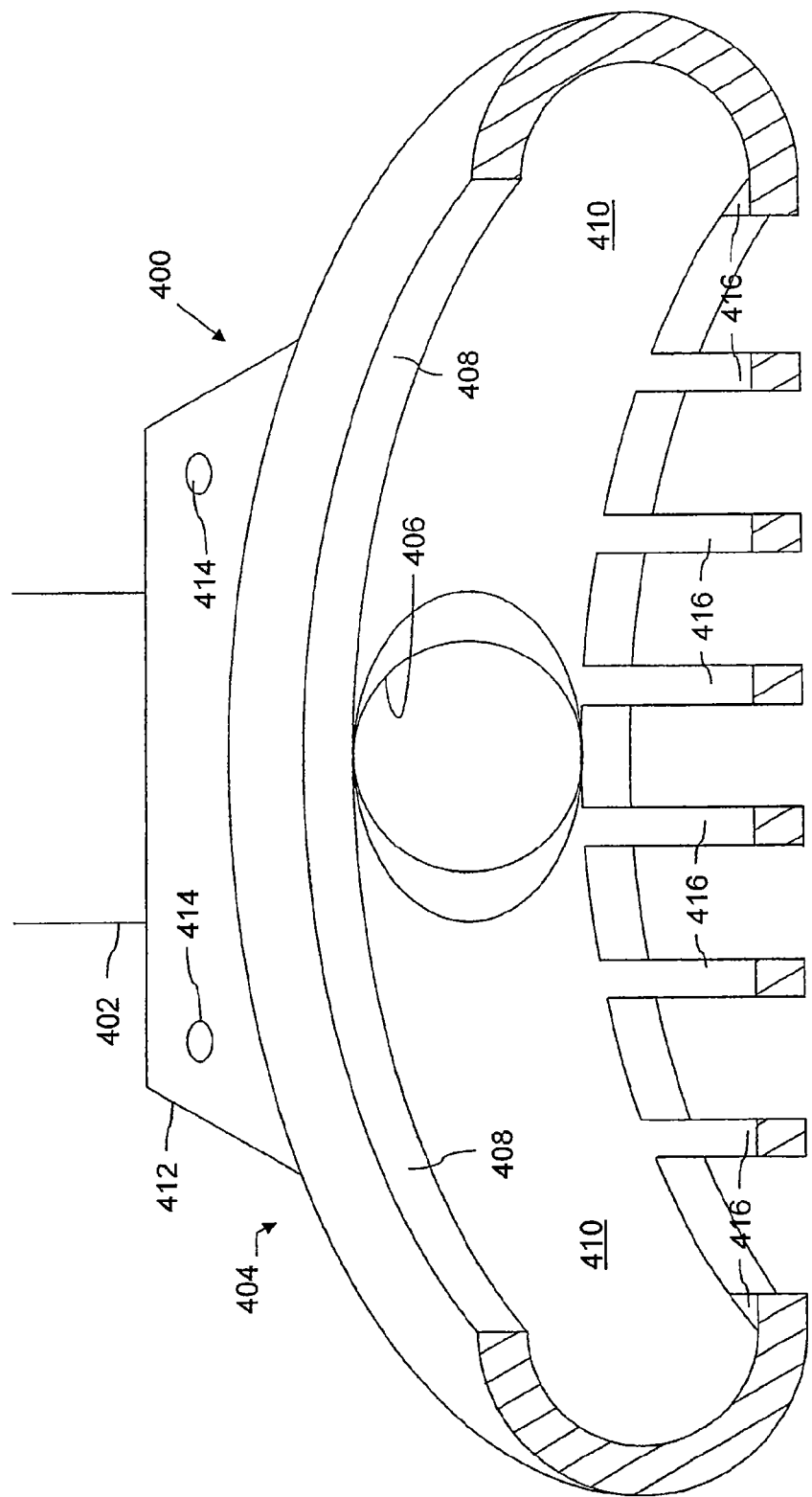
FIG. 20 is a cross section of the loop taken along lines 20-20 of FIG. 19.
Figure 21:
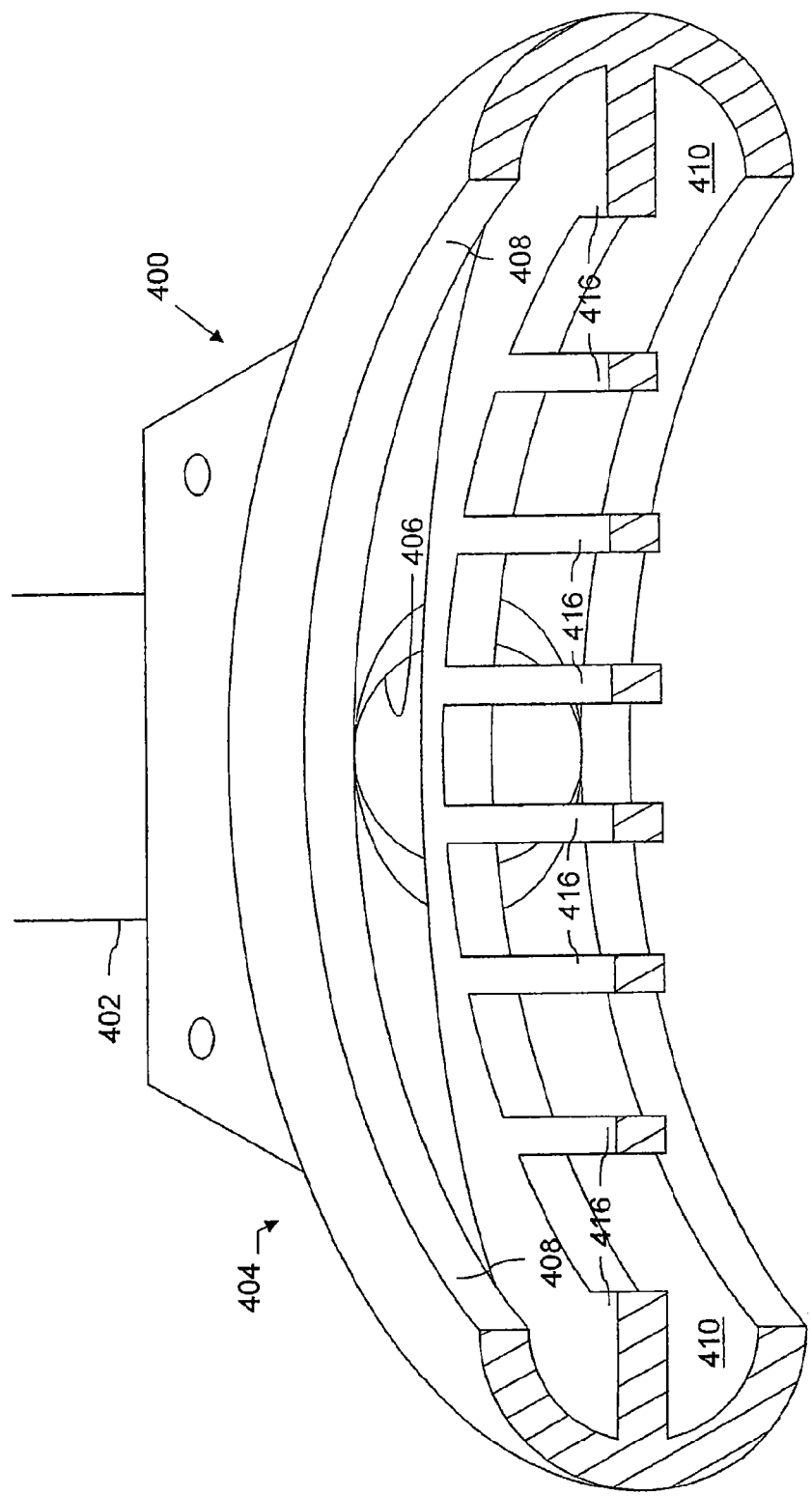
FIG. 21 is a cross section of an alternate embodiment of the loop taken along lines 20-20 of FIG. 19.

FIGS. 19-21 show an alternative embodiment of implant 400. This embodiment shows an alternative means of interconnecting loop 404 with conduit 402. An attachment structure 412 interconnects loop 404 with conduit 402. In one embodiment, attachment structure 412 includes suture holes 414. Although the figures show only two suture holes, any number of suture holes may be used.

Additionally, in this embodiment, implant 400 further includes bridges 416 affixed within loop 404. Bridges 416 may be of any size, shape, or pattern and may be positioned anywhere within loop 404. Additionally, any number of bridges 416 may be positioned within loop 404. Furthermore, loop 404 may be characterized as an exterior rim. In this characterization, it is the exterior rim that is interconnected with conduit 402. Like loop 404, the exterior rim may be interconnected with, or carried by, conduit 402 in any manner.

As should be understood, implant 400 may be implemented with any combination of bridges 416 and attachment structure 412.

The present invention provides a post-surgical ability to customize the implant by increasing its surface area, without the need of further surgery or an additional implant, by simply removing a ligature or series of ligatures after post-surgical intraocular pressure has been determined. This results in increased flow of aqueous humor and reduced intraocular pressure.

Another advantage of the present invention is that it provides an anchor for the implant, which is attachable to the sclera at the limbus. This has the advantage of preventing migration of the implant into the anterior chamber.

Another advantage of the present invention is that it provides a further three-fold reduction in bleb diameter resulting in a capsule only one cell layer thick, with the advantage that the resultant structure approaches the dimensions of the trabecular meshwork in a human eye.

Another advantage of the present invention is that it provides a post-surgical ability to customize the total surface area of the implant by increasing filtration surface area without the need of further surgery or an additional implant by simply removing, after post-surgical intraocular pressure has been determined, a ligature or series of ligatures located at intact portions along the length of the insert situated between C-shaped, open, cross-sectional portions.

Another advantage of the present invention is that it provides an implant with a resultant reduced surface tension on the wall of the implant with the advantage that fibrosis is minimized, thereby allowing continuous and on-going hydraulic conductivity of aqueous with a concomitant reduction in intraocular pressure to a safe and stabilized level.

Another advantage of the present invention is that it provides an implant nidus with a scalloped cross-section whereby separation of the fibrous tissue of the bleb from the implant nidus is facilitated and the cross-sectional dimension of the nidus may be reduced as compared to a smooth, round surface.

Another advantage of the present invention is that it provides a method for reducing intraocular pressure by creating a cylindrical bleb for producing improved accessory filtration by implanting a cylindrical tube having a proximal end and distal end, the distal portion of the cylindrical tube side wall being removed, into an eye to serve as a nidus for tissue deposition that can be changed into a conduit of aqueous humor to bypass angle structures and filter aqueous to orbital tissue and the blood supply.

While the above description contains many specificities, these should not be construed as limitations of the scope of the invention, but rather as an exemplification of preferred embodiments thereof. Many other variations are possible. For example, the material of the insert may be made of many types of elastomers other than silicone; the size of the needle may be other than 27 gauge; the size, number, shape and dimensions of nidi and slip knot ligatures may vary and is not limited to four or to a "C" shape; the open diameter of the implant could vary; and the shape of the implant could be other than circular in cross section. The term "slip knot" as used here and in the claims includes any releasable knot. A permanent suture can be used with the ligature release performed by laser lysis or ablation. Accordingly, the scope of the invention should be determined not by the embodiments illustrated, but by the appended claims and their legal equivalents.

What is claimed is:

1. A tube for implantation into the eye for conducting aqueous humor from a chamber of the eyeball to subconjunctival tissue comprising:
    an elongated fluid conducting conduit having a distal and a proximal end, a sidewall and an interior passageway,
    wherein said distal end is bifurcated and comprises a pair of bifurcated portions, each of the pair of bifurcated portions is a nidus configured for formation of a cylindrical aqueous filtration bleb along a longitudinal direction of each of the pair of bifurcated portions.

2. The tube of claim 1, further comprising at least one releasable ligature circumscribing the conduit.

3. The tube of claim 2, wherein the at least one releasable ligature is positioned between the proximal end and the distal end.

4. The tube of claim 1, further comprising at least one anchoring structure for attaching the tube to the sclera to prevent the tube from migrating from its placement site.

5. A method of conducting aqueous humor from a chamber of the eyeball to subconjunctival tissue comprising:
    implanting into the eye a tube according to claim 1; and
    allowing scar tissue to form at each bifurcation.

6. The method of claim 5, wherein the tube further comprises at least one releasable ligature circumscribing the conduit.

7. The method of claim 6, wherein the releasable ligature is positioned between the proximal end and the distal end.

8. The method of claim 5, wherein the tube further comprises at least one anchoring structure for attaching the tube to the sclera to prevent the tube from migrating from its placement site.

9. The method of claim 5, further comprising implanting the tube in the eye and anchoring the tube into the sclera of the eye, wherein scar tissue surrounds the nidus comprising each bifurcation.

* * * * *